(12) United States Patent
Chen

(10) Patent No.: US 12,622,725 B2
(45) Date of Patent: May 12, 2026

---

(54) CT-GUIDED PERCUTANEOUS PULMONARY NODULE CUTTER AND USING METHOD THEREOF

(71) Applicant: Mailin Chen, Beijing (CN)

(72) Inventor: Mailin Chen, Beijing (CN)

( * ) Notice: Subject to any disclaimer, the term of this patent is extended or adjusted under 35 U.S.C. 154(b) by 482 days.

(21) Appl. No.: 18/333,576

(22) Filed: Jun. 13, 2023

(65) Prior Publication Data

US 2024/0293146 A1 Sep. 5, 2024

(30) Foreign Application Priority Data

Mar. 3, 2023 (CN) ......................... 202310197984.6

(51) Int. Cl.
*A61B 17/34* (2006.01)

(52) U.S. Cl.
CPC ...... *A61B 17/3403* (2013.01); *A61B 17/3417* (2013.01); *A61B 17/3421* (2013.01); *A61B 17/3498* (2013.01); *A61B 2017/3405* (2013.01); *A61B 2017/3454* (2013.01); *A61B 2017/3456* (2013.01)

(58) Field of Classification Search
CPC ............ A61B 17/3403; A61B 17/3417; A61B 17/3421; A61B 17/3498; A61B 2017/3405; A61B 2017/3454; A61B 2017/3456; A61B 18/1492; A61B 2018/144; A61B 10/0283; A61B 18/14; A61B 18/149; A61B 2010/045; A61B 2018/00541; A61B 2018/00601; A61B 2018/00982; A61B 2090/3762; A61B 10/04
See application file for complete search history.

(56) References Cited

U.S. PATENT DOCUMENTS

| | | | |
|---|---|---|---|
| 2004/0010206 A1* | 1/2004 | Dubrul | A61B 17/221 600/567 |
| 2005/0070818 A1* | 3/2005 | Mueller | A61B 10/0275 600/564 |
| 2016/0157843 A1* | 6/2016 | Dickson | A61B 17/00234 606/47 |

* cited by examiner

*Primary Examiner* — Abid A Mustansir
(74) *Attorney, Agent, or Firm* — Hemisphere Law, PLLC

(57) ABSTRACT

A computed tomography-guided (CT-guided) percutaneous pulmonary nodule cutter includes an outer sheath puncture guide needle and a mesh-shaped electromagnetic cutting system; a hollow sleeve is disposed in the outer sheath puncture guide needle, and the mesh-shaped electromagnetic cutting system is disposed in a space between the outer sheath puncture guide needle and the hollow sleeve, a main body of the mesh-shaped electromagnetic cutting system is made of a polymer shape memory material into a tubular shape; and the tubular shape is integrally formed with two meshes at a position facing a tip end of the outer sheath puncture guide needle. By using the CT-guided percutaneous pulmonary nodule cutter, the patient's economic burden is reduced and the patient's comfort is improved and it is beneficial for promoting CT-guided percutaneous cutting biopsy of the pulmonary nodules.

6 Claims, 4 Drawing Sheets

CT-GUIDED PERCUTANEOUS PULMONARY NODULE CUTTER AND USING METHOD THEREOF

TECHNICAL FIELD

The disclosure relates to the technical field of a pulmonary nodule cutter, and particularly to a computed tomography-guided (CT-guided) percutaneous pulmonary nodule cutter and a using method thereof.

BACKGROUND

At present, computed tomography (CT) has found an increasing number of pulmonary nodules with a size less than 10 mm in the lungs, and there are many uncertain pulmonary nodules that require tissue biopsy to determine diagnosis, prognosis, and guide further treatment. However, a commonly used lung biopsy technique in clinic, such as a CT-guided percutaneous puncture, bronchoscopy, thoracoscopy or thoracotomy, has certain shortcomings for a biopsy of the pulmonary nodules, either a diagnostic efficacy is limited, or an invasive trauma is large and a risk is high, and safety, applicability or effectiveness of the commonly used lung biopsy technique affects the biopsy of the pulmonary nodules, and also affect results of pathological testing to a certain extent. At present, there is no safe and effective minimally invasive method or approach suitable for the biopsy of the pulmonary nodules.

Therefore, a CT-guided percutaneous pulmonary nodule cutter and a using method of the CT-guided percutaneous pulmonary nodule cutter are provided.

SUMMARY

A main purpose of the disclosure is to provide a CT-guided percutaneous pulmonary nodule cutter and a using method of the CT-guided percutaneous pulmonary nodule cutter, which is intended to solve or improve at least one of raised in the above-mentioned background technology.

In order to achieve the above purpose, the disclosure provides a CT-guided percutaneous pulmonary nodule cutter, which includes an outer sheath puncture guide needle and a mesh-shaped electromagnetic cutting system, a hollow sleeve disposed in the outer sheath puncture guide needle, and the mesh-shaped electromagnetic cutting system is disposed in a space between the outer sheath puncture guide needle and the hollow sleeve, a main body of the mesh-shaped electromagnetic cutting system is made of a polymer shape memory material into a tubular shape; and the tubular shape is integrally formed with two meshes at a position facing a tip end of the outer sheath puncture guide needle. An inner side of the tubular shape is provided with two metal wires, first ends of the two metal wires are correspondingly disposed at ends of the two meshes and extend out of the two meshes, and second ends of the two metal wires are disposed outside another end of the outer sheath puncture guide needle and correspondingly connected to a positive pole and a negative pole of a power supply through an excitation switch.

According to the CT-guided percutaneous pulmonary nodule cutter provided in the disclosure, a tail end of the hollow sleeve is connected to a negative pressure suction pump, and the negative pressure suction pump generates a negative pressure at a front end of the hollow sleeve.

According to the CT-guided percutaneous pulmonary nodule cutter provided in the disclosure, in an initial state, the two meshes merge to form a spherical cavity shape, and in an actual use state, the two meshes are squeezed and inserted into the space between the outer sheath puncture guide needle and the hollow sleeve and are pushed to a cutting point, when the compressed and deformed meshes are extended outside, the compressed and deformed meshes gradually return the spherical cavity shape to fix cut pulmonary nodules, after cut is completed, a removal of the pulmonary nodules is achieved in conjunction with the negative pressure suction fixation at the front end of the hollow sleeve.

The disclosure further provides a using method of the CT-guided percutaneous pulmonary nodule cutter, including the following steps:

(1) sleeving the outer sheath puncture guide needle with a chest wall duct dilator, and locating the outer sheath puncture guide needle at an edge of the pulmonary nodules through percutaneous puncture;

(2) inserting the hollow sleeve and the mesh-shaped electromagnetic cutting system to the edge of the pulmonary nodules;

(3) turning on a negative pressure switch and the mesh-shaped electromagnetic cutting system, and moving the mesh-shaped electromagnetic cutting system;

(4) activating the mesh-shaped electromagnetic cutting system and cutting off pulmonary tissue (i.e., pulmonary nodules) after observing an entry of the pulmonary nodules into the two meshes; and (5) returning the outer sheath puncture guide needle and the chest wall duct dilator, and removing a sample of the pulmonary nodules.

The disclosure discloses the following technical effects:

The purpose of the disclosure is to solve problems of pathological sampling of pulmonary nodules and to ensure comforts of patients, safety of doctors' operation, and effectiveness of pathological material collection. The medical personnel engaged in puncture biopsy can operate the CT-guided percutaneous pulmonary nodule cutter, the operation with the CT-guided percutaneous pulmonary nodule cutter is simple and easy, and positioning with the CT-guided percutaneous pulmonary nodule cutter is safe and accurate, so that a success rate of pathological diagnosis of the pulmonary nodules is significantly improved. The patient's economic burden can be reduced and the patient's comforts can be improved, and it is also beneficial for promoting CT-guided percutaneous cutting biopsy of the pulmonary nodules.

BRIEF DESCRIPTION OF DRAWINGS

In order to more clearly illustrate the technical solutions in the embodiments of the disclosure or in the prior art, the following is a brief description of the drawings to be used in the embodiments, it is obvious that the drawings in the following description are only some of the embodiments of the disclosure, and other drawings can be obtained according to these drawings without creative work for those of ordinary skill in the art.

DESCRIPTION OF REFERENCE NUMERALS

1. Outer sheath puncture guide needle; 2. Mesh-shaped electromagnetic cutting system; 3. Metal wire; 4. Hollow sleeve; 5. Chest wall duct dilator.

DETAILED DESCRIPTION OF EMBODIMENTS

The following will provide a clear and complete description of the technical solution in the embodiments of the disclosure, in conjunction with the accompanying drawings. Obviously, the described embodiments are only some of the embodiments of the disclosure, not all of them. Based on the embodiments in the disclosure, all other embodiments obtained by those skilled in the art without creative labor fall within the scope of protection of the disclosure.

Figure 1:
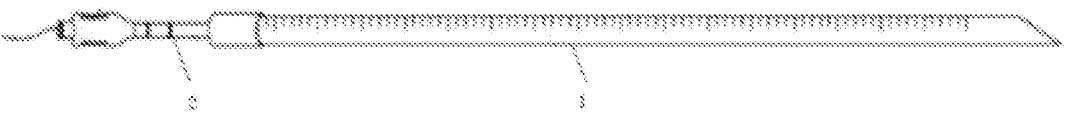
FIG. 1 is a schematic structural diagram of a CT-guided percutaneous pulmonary nodule cutter of the disclosure.
Figure 2:
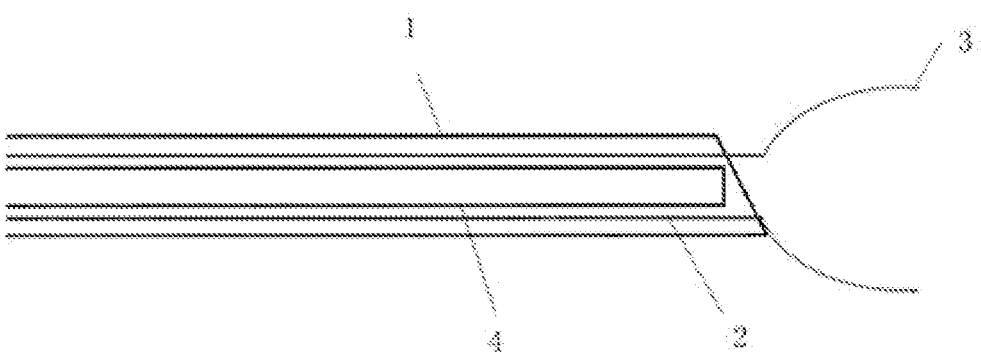
FIG. 2 is a schematic structural diagram of the two meshes extending partly of the disclosure.
Figure 3:
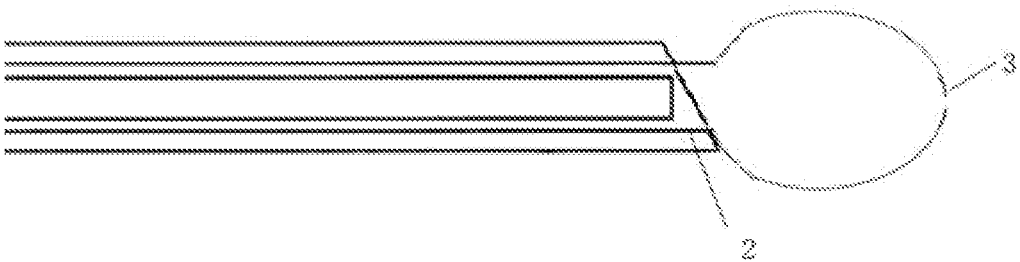
FIG. 3 is a schematic structural diagram of the two meshes extending fully of the disclosure.
Figure 4:
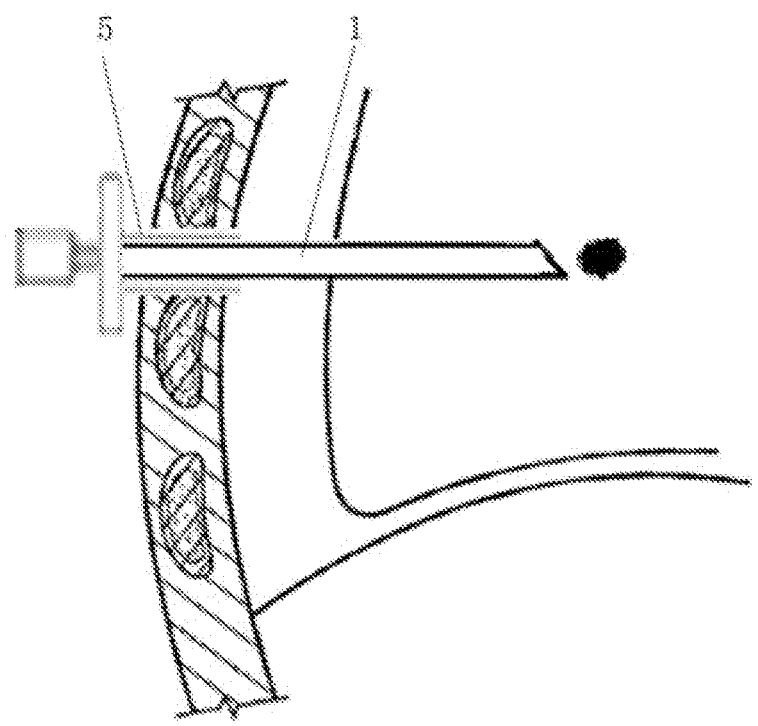
FIG. 4 is a schematic structural diagram of a first step when the CT-guided percutaneous pulmonary nodule cutter is used.
Figure 5:
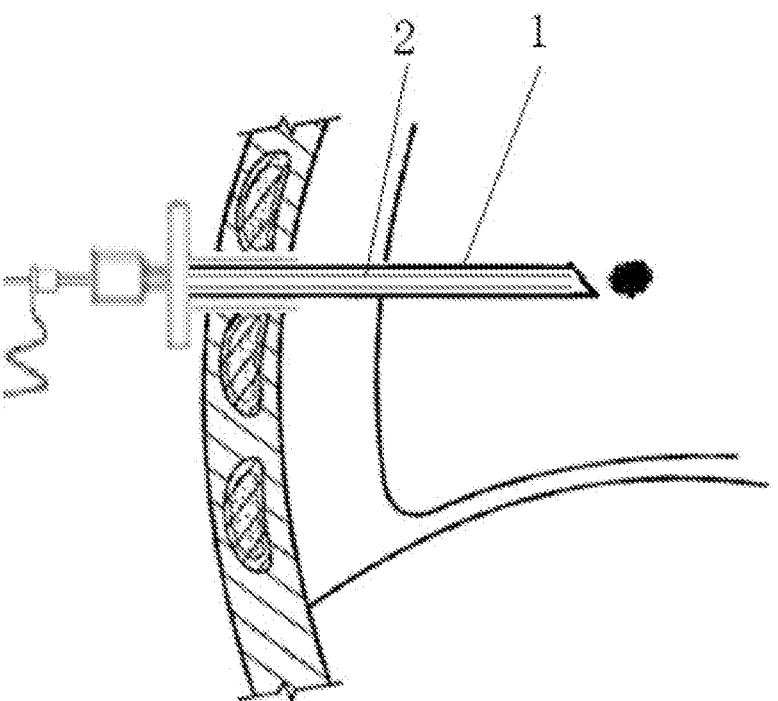
FIG. 5 is a schematic structural diagram of a second step when the CT-guided percutaneous pulmonary nodule cutter is used.
Figure 6:
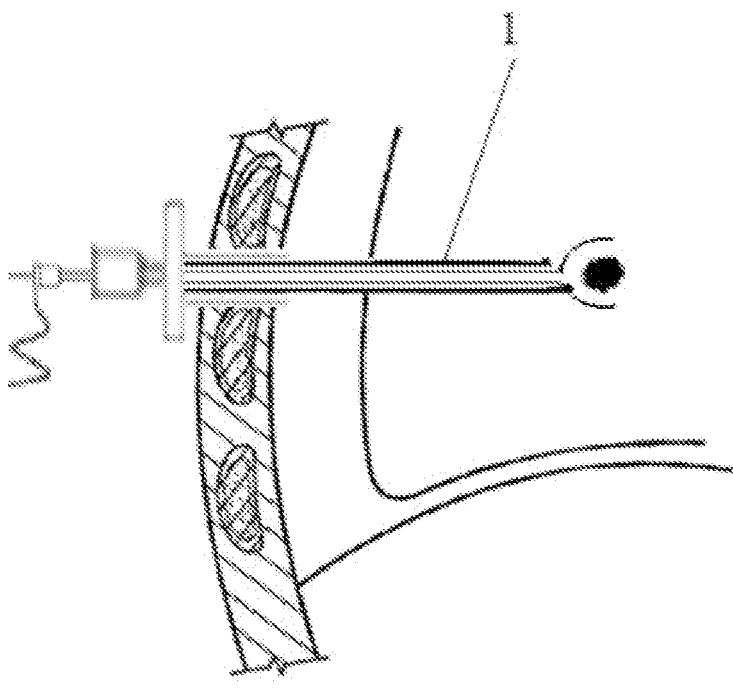
FIG. 6 is a schematic structural diagram of a third step when the CT-guided percutaneous pulmonary nodule cutter is used.
Figure 7:
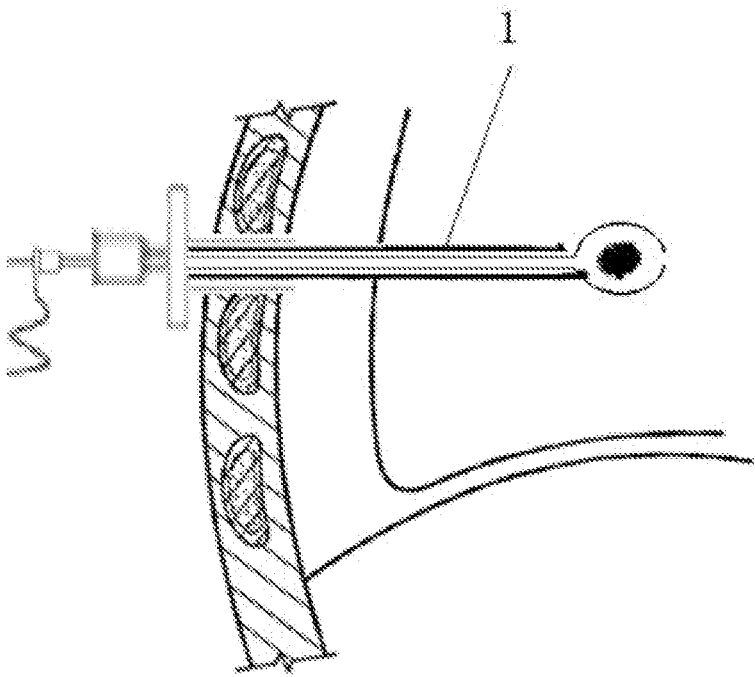
FIG. 7 is a schematic structural diagram of a forth step when the CT-guided percutaneous pulmonary nodule cutter is used.
Figure 8:
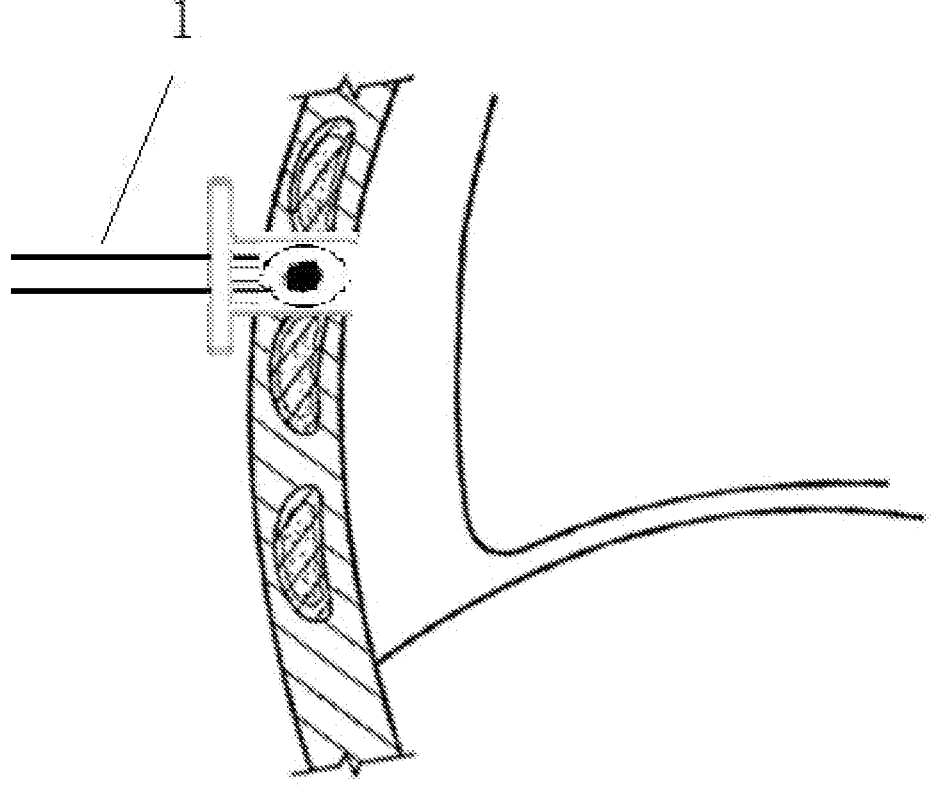
FIG. 8 is a schematic structural diagram of a fifth step when the CT-guided percutaneous pulmonary nodule cutter is used.

In order to make the above purposes, features, and advantages of the disclosure more apparent and understandable, the following will provide further detailed explanations of the disclosure in conjunction with the accompanying drawings and specific implementation methods Referring to FIGS. 1 to 8, the disclosure provides a CT-guided percutaneous pulmonary nodule cutter, which includes an outer sheath puncture guide needle 1 and a mesh-shaped electromagnetic cutting system 2, a hollow sleeve 4 disposed in the outer sheath puncture guide needle 1, the mesh-shaped electromagnetic cutting system 2 is disposed in a space between the outer sheath puncture guide needle 1 and the hollow sleeve 4, a main body of the mesh-shaped electromagnetic cutting system 2 is made of a polymer shape memory material into a tubular shape; and the tubular shape is integrally formed with two meshes at a position facing towards a tip end of the outer sheath puncture guide needle 1. An inner side of the tubular shape is provided with two metal wires 3, first ends of the two metal wires 3 are correspondingly disposed at ends of the two meshes and extend out of the two meshes, and second ends of the two metal wires are disposed outside another end of the outer sheath puncture guide needle 1 and correspondingly connected to a positive pole and a negative pole of a power supply through an excitation switch (Not shown in the figure).

In the embodiment, the outer sheath puncture guide needle 1 is used to locate at an edge of pulmonary nodules. By maintaining a contact between ends of the two meshes and a position of the pulmonary nodules, and then cooperating with the power supply to make the positive pole and the negative pole discharge to achieve a cutting. An electric cutting can reduce risks of bleeding, and when there is a bleeding, electrocoagulation can be performed, which has a great safety.

In the embodiment, an outer surface of the outer sheath puncture guide needle 1 is provided with a graduated scale, which facilitates doctors to visually observe an insertion depth, improves a convenience of a use process, and provides convenience for a surgical process. A head end of the outer sheath puncture guide needle 1 is a puncture tip, which is convenient for rapid penetration into an affected area. The outer sheath puncture guide needle 1 is a hollow structure, and a connector is disposed on a surface corresponding to a tail end of the outer sheath puncture guide needle 1, which is used to connect a safety handle, in the embodiment, the excitation switch (Not shown in the figure) is fixed to the safety handle, which facilitates doctors to operate. An outer surface of the safety handle is provided with an anti-slide structure to prevent slipping during operation and improve safety performance.

The disclosure is to solve problems of pathological sampling of the pulmonary nodules and the effectiveness of the pathological sampling, ensuring comforts of patients and safety of doctors' operation. The medical personnel engaged in puncture biopsy can operate the CT-guided percutaneous pulmonary nodule cutter, the operation with the CT-guided percutaneous pulmonary nodule cutter is simple and easy, and positioning with the CT-guided percutaneous pulmonary nodule cutter is safe and accurate, so that a success rate of pathological diagnosis of the pulmonary nodules is significantly improved. The patient's economic burden can be reduced and the patient's comforts can be improved, and it is also beneficial for promoting CT-guided percutaneous cutting biopsy of the pulmonary nodules.

In a further embodiment, a tail end of the hollow sleeve 4 is connected to a negative pressure suction pump (Not shown in the figure), a model of the negative pressure suction pump can be chosen according to a specific usage environment, and there are no specific limitations in the embodiment. The tail end of the hollow sleeve 4 is provided with a conversion head, the conversion head is detachably connected with a negative pressure hose, on the one hand, the negative pressure hose is used to connect the negative pressure suction pump and generate a negative pressure for a surgical process, on the other hand, the negative pressure hose can be used to be passed through by a power line of the mesh-shaped electromagnetic cutting system 2 and provide a cover protection for the power line.

In an using state, the negative pressure suction pump (not shown in the figure) generates the negative pressure at a front end of the hollow sleeve 4 to attract the cut pulmonary nodules, avoiding the cut pulmonary nodules from slipping during a removal process, realizing the effective removal of the pulmonary nodules, improving the work efficiency, shortening time for a precise resection surgery, and reducing a surgical risk.

In a further embodiment, in a natural state, two meshes merge to form a spherical cavity shape. In an actual use state, the two meshes are squeezed and inserted into the space between the outer sheath puncture guide needle 1 and the hollow sleeve 4 and are pushed to a cutting point, when the compressed and deformed meshes are extended outside, the compressed and deformed meshes gradually return the spherical cavity shape to fix the cut pulmonary nodules, after the cut is completed, a removal of the pulmonary nodules is achieved in conjunction with the negative pressure suction fixation at the front end of the hollow sleeve 4.

In the embodiment, the two meshes of the mesh-shaped electromagnetic cutting system 2 form an ellipsoidal shape when the two meshes are closed as a whole. And an end of the mesh-shaped electromagnetic cutting system 2 enters a cutting point along with the outer sheath puncture guide needle 1, a middle of the two meshes is compressed, ends of the two meshes are opened, making it easy to wrap and fix the cut pulmonary nodules.

The CT-guided percutaneous pulmonary nodule cutter is an umbrella-shaped negative pressure electric cutting device.

The disclosure further provides a using method of the CT-guided percutaneous pulmonary nodule cutter including the following steps (1) to (5).

At step (1), sleeving the outer sheath puncture guide needle 1 with a chest wall duct dilator 5, and locating the outer sheath puncture guide needle 1 at an edge of the pulmonary nodules through percutaneous puncture.

At step (2), inserting the hollow sleeve 4 and the mesh-shaped electromagnetic cutting system 2 to the edge of the pulmonary nodules.

At step (3), turning on a negative pressure switch and the mesh-shaped electromagnetic cutting system 2, and moving the mesh-shaped electromagnetic cutting system forward slowly. A forward distance can be set according to a specific usage environment, in the embodiment, the forward distance does not exceed 10 mm. The forward distance can be directly observed through the graduated scale on the outer surface of the sheath puncture guide needle 1. By turning on the negative pressure switch to provide the negative pressure, after the cut of the pulmonary nodules is completed, a removal of the pulmonary nodules is achieved in conjunction with the negative pressure suction fixation at the top end of the hollow sleeve 4.

At step (4), activating the mesh-shaped electromagnetic cutting system 2 and cutting off pulmonary tissue after observing an entry of the pulmonary nodules into the meshes of the mesh-shaped electromagnetic cutting system 2.

At step (5), returning the outer sheath puncture guide needle 1 and the chest wall duct dilator 5, and removing a sample of the pulmonary nodules.

In the description of the disclosure, it should be understood that the terms "longitudinal", "transverse", "up", "down", "front", "back", "left", "right", "vertical", "horizontal", "top", "bottom", "inside", "outside", and other indications of orientation or positional relationships are based on the orientation or positional relationships shown in the accompanying drawings, solely for the convenience of describing the disclosure, rather than indicating or implying that the device or component referred to must have a specific orientation, be constructed and operated in a specific orientation, therefore it cannot be understood as a limitation of the disclosure.

Although the disclosure has been described in detail with reference to the aforementioned embodiments, it is still possible for those skilled in the art to modify the technical solutions recorded in the aforementioned embodiments, or to equivalently replace some of the technical features. Any modifications, equivalent replacements, improvements, etc. made within the essence and principles of the disclosure shall be included in the scope of protection of the disclosure.

What is claimed is:

1. A percutaneous pulmonary nodule cutter comprises:
an outer sheath puncture guide needle,
a hollow sleeve disposed in the outer sheath puncture guide needle, and
a mesh-shaped electromagnetic cutting system disposed in a space between the outer sheath puncture guide needle and the hollow sleeve;
wherein a main body of the mesh-shaped electromagnetic cutting system is made of a polymer shape memory material into a tubular shape, the tubular shape is integrally formed with two meshes at a position facing towards a tip end of the outer sheath puncture guide needle, an inner side of the tubular shape is provided with two metal wires, first ends of the two metal wires are correspondingly disposed at ends of the two meshes and extend out of the two meshes, and second ends of the two metal wires are disposed outside another end of the outer sheath puncture guide needle and correspondingly connected to a positive pole and a negative pole of a power supply through an excitation switch.

2. The percutaneous pulmonary nodule cutter as claimed in claim 1, wherein a tail end of the hollow sleeve is connected to a negative pressure suction pump, and the negative pressure suction pump is configured to generate a negative pressure at a front end of the hollow sleeve.

3. The percutaneous pulmonary nodule cutter as claimed in claim 2, the tail end of the hollow sleeve is provided with a conversion head, the conversion head is detachably connected with a negative pressure hose, and the negative pressure hose is connected with the negative pressure suction pump.

4. The percutaneous pulmonary nodule cutter as claimed in claim 1, wherein in an initial state, the two meshes merge to form a spherical cavity shape; and in an actual use state, the two meshes are squeezed and inserted into the space between the outer sheath puncture guide needle and the hollow sleeve and are pushed to a cutting point, when the compressed and deformed meshes are extended outside, the compressed and deformed meshes gradually return the spherical cavity shape to fix cut pulmonary nodules, and the pulmonary nodules are removed in conjunction with a negative pressure suction fixation at the front end of the hollow sleeve after cut is completed.

5. The percutaneous pulmonary nodule cutter as claimed in claim 1, wherein an outer surface of the outer sheath puncture guide needle is provided with a graduated scale.

6. The percutaneous pulmonary nodule cutter as claimed in claim 1, wherein a connector is disposed on a surface corresponding to a tail end of the outer sheath puncture guide needle, the connector is configured to connect a handle, and an outer surface of the handle is provided with an anti-slide structure.

* * * * *